US005628848A

United States Patent [19]
Friese et al.

[11] Patent Number: 5,628,848
[45] Date of Patent: May 13, 1997

[54] PROCESS FOR THE PRODUCTION OF COMPOSITE SYSTEMS HAVING AT LEAST TWO INORGANIC CERAMIC LAYERS

[75] Inventors: Karl-Hermann Friese, Leonberg; Werner Gruenwald, Gerlingen; Ulrich Eisele, Stuttgart, all of Germany

[73] Assignee: Robert Bosch GmbH, Stuttgart, Germany

[21] Appl. No.: 367,141

[22] PCT Filed: May 6, 1994

[86] PCT No.: PCT/DE94/00520
§ 371 Date: Jan. 9, 1995
§ 102(e) Date: Jan. 9, 1995

[87] PCT Pub. No.: WO94/27819
PCT Pub. Date: Dec. 8, 1994

[30] Foreign Application Priority Data

May 22, 1993 [DE] Germany ............... 43 17 174.5

[51] Int. Cl.[6] ................................... B32B 31/26
[52] U.S. Cl. ............................... 156/89; 264/618
[58] Field of Search ................... 156/89; 264/60; 428/699, 701; 501/103

[56] References Cited

U.S. PATENT DOCUMENTS

| 4,428,895 | 1/1984 | Blasch et al. ............ 264/60 X |
|---|---|---|
| 4,501,818 | 2/1985 | Rossi ..................... 501/103 X |
| 4,767,479 | 8/1988 | Ferguson et al. .......... 264/60 X |
| 4,800,137 | 1/1989 | Okuno et al. ............. 156/89 X |
| 4,806,739 | 2/1989 | Kojima et al. . |
| 4,957,673 | 9/1990 | Schroeder et al. . |
| 5,026,601 | 6/1991 | Lio et al. ................ 428/701 X |

FOREIGN PATENT DOCUMENTS

| 0134136 | 3/1985 | European Pat. Off. . |
|---|---|---|
| 0166445 | 1/1986 | European Pat. Off. . |
| 0203351 | 12/1986 | European Pat. Off. . |
| 0263468 | 4/1988 | European Pat. Off. . |

Primary Examiner—David A. Simmons
Assistant Examiner—M. Curtis Mayes

[57] ABSTRACT

The invention relates to composite systems having at least two layers which comprise different inorganic, ceramic phases and are produced by cosintering of different, finely divided inorganic materials arranged in layers. The composite systems are characterized in that at least two adjacent layers comprise a dense phase largely free of macropores. The layers are durably bonded to one another by sintering together of particles of the different materials at the phase boundary or boundaries. The composite systems and the processes for the production thereof are used, for example, in the manufacture of gas sensors.

4 Claims, 1 Drawing Sheet

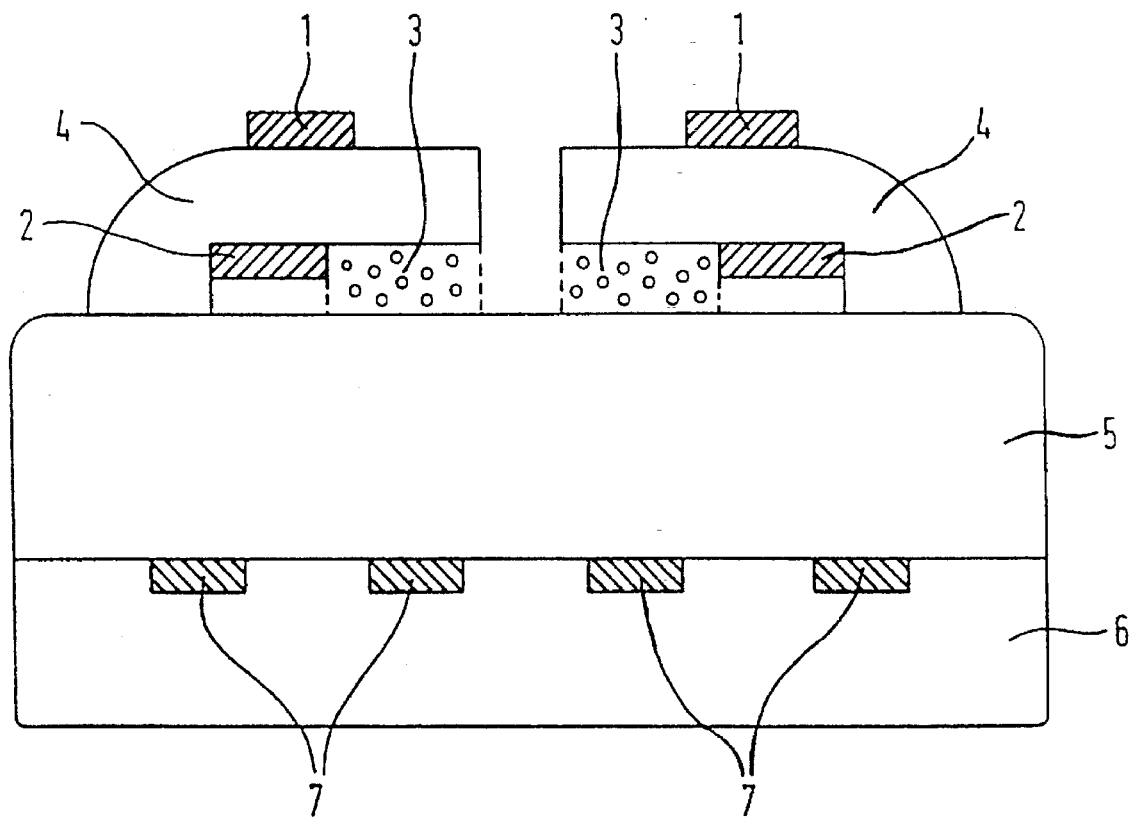

PROCESS FOR THE PRODUCTION OF COMPOSITE SYSTEMS HAVING AT LEAST TWO INORGANIC CERAMIC LAYERS

BACKGROUND OF THE INVENTION

Components containing composite systems having at least two flat or curved layers comprising different inorganic, ceramic phases are well known in industry. Examples which may be mentioned are gas sensors, such as are used for the measurement of carbon monoxide in exhaust gases of internal combustion engines, and also heating elements. The composite systems can be produced in a known manner by sintering finely divided inorganic materials in two or more stages, by first shaping and sintering the material which forms the first layer, then applying the material of the second layer onto the first sintered layer and again sintering and repeating this procedure until the desired number of layers has been reached. Owing to the many operations, this process is not optimum in terms of production technology. In addition, the adhesion of the layers not infrequently leaves something to be desired.

More advantageous is another known process in which the finely divided materials which form the various layers of the finished composite system are arranged in layers and sintered together. This process is also described as cosintering, and, in it, the bonding of the various layers is generally better than in the above-described process. Nevertheless, the composite bodies are frequently not completely satisfactory with regard to mechanical and thermal stressability, with thermal stressing being understood to include frequent change between cold and hot operating states. The stresses occurring during this process can lead to the formation of cracks and to detachment of parts of the composite body.

U.S. Pat. No. 4,806,739 discloses ceramic heaters produced by cosintering, in which heaters the heating element is separated by an aluminium oxide layer from a solid electrolyte comprising zirconium(IV) oxide. In column 2, lines 22 to 30, it is stated that a small amount of zirconium (IV) oxide in the aluminium oxide suppresses the tendency to shrink (or the shrinkage) of the layer and stronger bonding of the two layers is achieved.

European Patent 203 351 describes an oxygen sensor produced by cosintering, which sensor contains, between a layer of a solid electrolyte, namely zirconium(IV) oxide, and an electrically insulating layer containing aluminium oxide as main constituent, an intermediate layer which reacts with the solid electrolyte and with the aluminium oxide of the insulating layer and whose linear coefficient of thermal expansion lies between those of the materials in the two layers mentioned (Claim 1). The intermediate layer advantageously comprises zirconium(IV) oxide which is partially stabilized with 6 mol per cent of yttrium oxide and contains 3 per cent by weight of aluminium oxide (column 8, lines 9 to 11). It reduces the stress which results from the different coefficients of thermal expansion of the two layers and which, without the intermediate layer, could destroy the oxygen sensor (column 7, lines 58 to 62). Furthermore, the intermediate layer is supposed to improve the bonding between the two layers, since zirconium(IV) oxide and aluminium oxide hardly react with one another (column 7, lines 62 to 64).

The patent further discloses that an inorganic binder comprising 30 per cent by weight of aluminium oxide, 53 per cent by weight of silicon dioxide and 17 per cent by weight of magnesium oxide is added to the aluminium oxide of the electrically insulating layer (column 6, lines 54 to 60). Another suitable binder contains from 5 to 30 per cent by weight of aluminium oxide and from 70 to 95 per cent by weight of silicon dioxide (column 7, lines 37 to 39). The binder is supposed to melt below the sintering temperature of the aluminium oxide, accelerate the sintering of the aluminium oxide and counteract the shrinkage during cosintering with zirconium(IV) oxide (column 7, lines 20 to 36). At the same place it is stated, without further elaboration, that the shrinkage during sintering can also be counteracted by matching the particle size distribution of the zirconium(IV) oxide and the aluminium oxide.

SUMMARY OF THE INVENTION

The composite systems of the invention can, in terms of production technology, be favourably produced by cosintering. The layers comprise a dense phase largely free of macropores and are therefore able to be highly stressed mechanically. They are bonded to one another so strongly that they can hardly be separated from one another without destroying the layers. Surprisingly, the composite systems of the invention are also extraordinarily thermally stable. They survive numerous changes between cold and hot states without stresses leading to detachment of parts of the composite system or even to the destruction thereof. This result is achieved without a compensating intermediate layer and without addition of binders or other additives.

BRIEF DESCRIPTION OF THE DRAWING

The sole drawing FIGURE shows, in section, a sensor for determining oxygen in lean exhaust gases, which according to the invention has a dense, essentially macropore-free substrate formed from nanosize aluminium oxide and also a likewise dense and essentially macropore-free layer strongly bonded thereto by cosintering, which layer is formed from zirconium(IV) oxide having particle sizes in the micron range.

DESCRIPTION OF THE PREFERRED EMBODIMENTS

The advantages described above are possessed by the claimed composite systems, which have been produced according to the claimed processes. The invention is based on the observation that composite systems having at least two inorganic ceramic layers can be highly stressed mechanically and thermally and are extraordinarily strongly bonded to one another if the adjacent phases are dense, i.e., largely free of macropores. Preference is given to composite systems having oxidic layers.

The composite systems can have two layers, but it is also possible to produce composite systems having from 3 to 5 and more layers by the process of the invention. The ceramic phases can be oxidic or comprise other inorganic materials, such as nitrides, carbides and/or borides. Mixed phases are also possible, for example, of nitrides and carbides.

The finely divided inorganic materials which form the layers of the composite system generally have the same chemical composition as the sintered layers. However, it is also possible to start with materials which change on heating, for example, from a mixture of aluminium oxide with aluminium hydroxide and/or magnesium carbonate. The sintering process occurs sufficiently slowly for the eliminated water and carbon dioxide to be able to escape.

It is an important feature of the invention that at least one of the different finely divided materials, from which the composite system is formed, comprises particles having a mean particle diameter in the nanometer range. Naturally it is also possible for the mean particle sizes of a plurality of finely divided inorganic starting materials to lie in the nanometer range, with the corresponding layers being able to be adjacent or separated by other layers. Preference is given to composite systems having adjacent dense oxidic phases of which one is formed from nanosize powder and the other is formed from powder having mean particle sizes in the micron range.

Another important feature of the invention is that the mean particle size of the finely divided inorganic material in the nanometer range, which forms a particular layer of the composite system, is matched to the mean particle size of a finely divided inorganic material which forms the adjacent layer in such a way that the two resulting adjacent ceramic phases are dense and virtually free of voids. The mean particle size of the nanosize finely divided inorganic material is here generally the variable parameter, although it is also possible, the other way round, to match the mean particle size of the material having particles in the micron range to a given mean particle size of the material in the nanometer range.

The feature "largely free of macropores" implies that the dense phases of the composite systems according to the invention may very well contain pores. For one thing, a sintered body is never compact in the strict sense. Sintering can be understood as a conversion of surfaces into interfaces, with small pores (micropores) always remaining. However, their diameter is smaller than the mean diameter of the particles. In addition, however, it is generally also possible to observe larger pores (macropores) whose diameters are greater than the mean diameter of the particles. These macropores, which are undesired because they reduce the quality, are difficult to avoid, even with strict monitoring of the process conditions. For the purposes of this invention, a layer is regarded as largely free of macropores if the proportion by volume of the pores having a diameter of more than the mean diameter of the finely divided inorganic material from which the layer is formed is not more than 4%, advantageously not more than 2% and in particular not more than 1%. The proportion by volume is determined by quantitative microscopy.

The mean particle diameters of the finely divided inorganic materials in the nanometer range are generally from 10 to 200 nm. They are determined by scanning or tunnel electron microscopy. The other finely divided inorganic materials are generally present in the degree of fineness customary for sintering technology, i.e., the mean particle diameter is in the micron range, for example, between 2.5 and 5.0 µm.

The finely divided inorganic materials used for the invention are well known to those skilled in the art. The preparation of finely divided oxidic materials having particle sizes in the nanometer range is described, for example, by R. Naβ et al in Eurogel '91, Elsevier Science Publishers B. V., pages 243 to 255. The authors give other literature references which describe the preparation of nanosize materials.

There is no known practically usable mathematical relationship which allows the mean particle diameter of the one finely divided inorganic material to be used to calculate the optimum mean particle diameter of the other finely divided inorganic material which forms an adjacent layer. Rather, this optimum mean particle diameter has to be determined by preliminary experiments. The rule which applies here is that the nanosize material used should be that finely divided inorganic material which, for a mean particle diameter in the conventional, i.e., micron, range, has a higher sintering temperature than another material intended for an adjacent layer and having a mean particle size which is likewise in the micron range. The mean particle size of the nanosize material should be all the smaller, the higher the sintering temperature of the corresponding microsize material lies above the sintering temperature of the other, likewise microsize, finely divided inorganic material.

The sintering temperature used in cosintering is generally in accordance with the lowest sintering temperature of the finely divided inorganic materials having mean particle diameters in the conventional, i.e. micron, range participating in the production of the composite system. Thus, the temperature is generally at from 900° to 1350° C. The time required for cosintering lies within the customary range and is generally from 1 to 30 hours.

The process is particularly suitable for the cosintering of layers of zirconium(IV) oxide, which can be fully or partially stabilized, with aluminium oxide. Composite systems having particularly good properties are obtained when the mean particle size of the finely divided aluminium oxide is between 50 and 200 nanometers and that of the zirconium (IV) oxide is between 0.5 and 2.0 microns.

The composite systems of the invention can be flat, planar structures or be curved, for example, have a cylindrical or conical shape. The process of the invention enables production of, for example, gas sensors for the determination of carbon monoxide in exhaust gases of internal combustion engines. Other components for the production of which the process of the invention is suitable are heating devices and temperature sensors. Composite systems of the invention or components containing such composite systems are produced by processes known per se. For example, the layers brought into apposition with one another prior to cosintering can be produced from finely divided inorganic materials by printing or sheet techniques.

EXAMPLE

The present invention is realized in a sensor for the determination of oxygen in lean exhaust gases according to the drawing. The sensor comprises a substrate or first layer 5 and a cover 6 which close the heater 7 and were both produced from nanosize aluminium oxide having a mean particle size of 90 nm. The solid electrolyte or second layer 4 comprises zirconium(IV) oxide and is formed from a powder having a mean particle size of 1.8 µm. The solid electrolyte 4 and the substrate 5 are strongly bonded to one another by cosintering (5 hours at 1300° C.). Between the roof-shaped solid electrolyte 4 and the substrate 5, there are located the cathode 2 and the diffusion resistance 3; on the solid electrolyte there is located the anode 1. The sensor has a high thermal and mechanical stressability even on frequent change between hot operating and cold rest states. The response sensitivity corresponds to that of conventional sensors of this type.

The same properties are shown by sensors in the production of which nanosize aluminium oxide having mean particles sizes of 14, 63 and 110 nm has been used.

What is claimed is:

1. A cosintering process for producing a ceramic composite structure having at least two ceramic layers which are durably bonded to one another and which are substantially free of macropores, comprising:
   a. providing a first layer which is comprised of a powder of a first ceramic material;

b. providing on the first layer a second layer which is comprised of a powder of a second ceramic material, the first and second ceramic materials having respective mean particle diameters in which the powder of the first ceramic material has a mean particle diameter in the nanometer range and the powder of the second ceramic material has a mean particle diameter in the micron range; and c. cosintering at least the first and second layers together at a sintering temperature which is the lowest sintering temperature effective to provide a predetermined density after sintering for the layers, wherein the first layer comprises aluminum oxide and the second layer comprises zirconium(IV) oxide, wherein the first and second ceramic materials are such that, if the mean particle diameters of the first and second ceramic materials were identical, the first and second layers would require different sintering temperatures to attain an essentially identical density after sintering, and the first layer would require a higher sintering temperature compared to that of the second layer, and wherein the respective particle sizes of the first and second ceramic materials are matched to enable cosintering by the second ceramic material having a mean particle diameter which is larger than that of the first ceramic material.

2. The process according to claim 1, wherein the first ceramic material has a mean particle size which ranges from 10 to 200 nm, and wherein the second ceramic material has a mean particle size which ranges from 0.5 to 5.0 μm.

3. The process according to claim 1, wherein the second layer is comprised of zirconium(IV) oxide and stabilizing agent.

4. The process according to claim 3, wherein the stabilizing agent is yttrium oxide and is present in an amount which is effective to at least partially stabilize the zirconium (IV) oxide.

* * * * *